United States Patent
Andrea et al.

(10) Patent No.: US 12,404,160 B2
(45) Date of Patent: Sep. 2, 2025

(54) APPARATUS FOR TREATING CLOSURES FOR CONTAINERS

(71) Applicant: GEA PROCOMAC S.p.A., Sala Baganza (IT)

(72) Inventors: Comani Andrea, Sala Baganza (IT); Abelli Paolo, Parma (IT)

(73) Assignee: GEA PROCOMAC S.p.A., Sala Baganza (IT)

( * ) Notice: Subject to any disclaimer, the term of this patent is extended or adjusted under 35 U.S.C. 154(b) by 76 days.

(21) Appl. No.: 18/491,545

(22) Filed: Oct. 20, 2023

(65) Prior Publication Data
US 2024/0158217 A1    May 16, 2024

(30) Foreign Application Priority Data
Nov. 10, 2022    (IT) .................. 102022000023250

(51) Int. Cl.
    *B67B 3/26*      (2006.01)
    *B67C 3/26*      (2006.01)

(52) U.S. Cl.
    CPC .................. *B67C 3/2642* (2013.01)

(58) Field of Classification Search
    CPC .................................... B67C 3/2642
    See application file for complete search history.

(56) References Cited

U.S. PATENT DOCUMENTS

| | | | | |
|---|---|---|---|---|
| 1,920,539 A | * | 8/1933 | White ................ | B65B 7/28 100/153 |
| 2,154,266 A | * | 4/1939 | Ferd ................ | B67B 3/24 100/154 |
| 3,766,709 A | * | 10/1973 | Zausner ............ | B65B 55/10 53/167 |

(Continued)

FOREIGN PATENT DOCUMENTS

| | | | | |
|---|---|---|---|---|
| CN | 101044098 A | * | 9/2007 | ............ C02F 1/78 |
| CN | 205019451 U | * | 2/2016 | |

(Continued)

OTHER PUBLICATIONS

Search Report received in connection with Italian Application No. 102022000023250 dated May 10, 2023.

*Primary Examiner* — Lucas E. A. Palmer
(74) *Attorney, Agent, or Firm* — Brian Parke

(57) ABSTRACT

A treatment apparatus for treating closures for containers. The treatment apparatus includes a box-like body and a treating chamber inside the box-like body. The treating chamber configured for treating the closures. The treatment apparatus further includes a dispensing pipe located inside the treating chamber and configured to dispense a sterilizing substance and a supplying circuit configured to supplying the sterilizing substance. The supplying circuit including a feeding line, a main line, and a secondary line. Both the main line and the secondary line branching-off from the feeding line and the main line emerging into the dispensing pipe and the secondary line emerging inside the box-like body. The (Continued)

treatment apparatus further includes one or more valves operatively active on the supplying circuit to establish a selective fluid communication between the feeding line and the main line or between the feeding line and the secondary line.

10 Claims, 4 Drawing Sheets

(56) References Cited

U.S. PATENT DOCUMENTS

| | | | | |
|---|---|---|---|---|
| 4,296,769 A * | 10/1981 | van der Lugt | ............ | B67B 1/03 |
| | | | | 118/316 |
| 4,327,826 A * | 5/1982 | Wilson | .................... | B65B 5/101 |
| | | | | 198/740 |
| 4,530,202 A * | 7/1985 | Powell | .................. | B67C 7/0073 |
| | | | | 141/90 |
| 5,022,165 A * | 6/1991 | Beswick | ................. | B65B 55/10 |
| | | | | 422/115 |
| 5,031,673 A * | 7/1991 | Clusserath | .............. | B67C 3/286 |
| | | | | 141/11 |
| 5,501,253 A * | 3/1996 | Weiss | .................... | B67C 3/2631 |
| | | | | 141/49 |
| RE37,471 E * | 12/2001 | Jagger | ................... | B65B 55/025 |
| | | | | 198/803.14 |
| RE38,747 E * | 6/2005 | Jagger | ................... | B65B 55/027 |
| | | | | 198/803.14 |
| 9,139,378 B2 * | 9/2015 | Lopez | .................. | B65G 47/256 |
| 9,150,398 B2 * | 10/2015 | Hartel | ....................... | B67C 3/20 |
| 9,205,937 B2 * | 12/2015 | Krulitsch | ................ | B67C 3/026 |
| 9,637,254 B2 * | 5/2017 | Fahldieck | ................. | B67C 3/26 |
| 9,809,436 B2 * | 11/2017 | Clüsserath | ................ | B67C 3/10 |
| 10,294,091 B2 * | 5/2019 | Eaton | ...................... | B67C 3/202 |
| 10,376,940 B2 * | 8/2019 | Wong | ...................... | B21C 43/02 |
| 10,905,786 B2 * | 2/2021 | Shodder | .................... | A61L 2/26 |
| 11,247,888 B2 * | 2/2022 | Knott | ........................ | B67C 3/06 |
| 11,325,817 B2 * | 5/2022 | Staeber | .................... | B65B 31/08 |
| 11,691,862 B2 * | 7/2023 | Poeschl | ..................... | B67C 3/26 |
| | | | | 141/1 |
| 2001/0045242 A1 * | 11/2001 | Clusserath | .............. | B67C 3/007 |
| | | | | 141/144 |
| 2010/0275955 A1 * | 11/2010 | Ueda | ......................... | A61L 2/07 |
| | | | | 134/131 |
| 2011/0142731 A1 * | 6/2011 | Beckmann | .............. | B67B 3/003 |
| | | | | 422/292 |
| 2011/0158846 A1 * | 6/2011 | Boschi | .................... | B67B 3/003 |
| | | | | 422/292 |
| 2011/0311399 A1 * | 12/2011 | Silvestri | .................... | A61L 2/22 |
| | | | | 422/292 |
| 2013/0004368 A1 * | 1/2013 | Morita | .................... | B67B 3/003 |
| | | | | 422/292 |
| 2013/0243648 A1 * | 9/2013 | Buchhauser | ............ | A61L 2/208 |
| | | | | 422/302 |
| 2017/0056541 A1 * | 3/2017 | Sveningsson | .............. | A61L 2/22 |
| 2022/0289546 A1 * | 9/2022 | Krulitsch | ................ | B67C 3/2642 |

FOREIGN PATENT DOCUMENTS

| | | |
|---|---|---|
| CN | 105979974 A | 9/2016 |
| CN | 116462148 A * | 7/2023 |

* cited by examiner

APPARATUS FOR TREATING CLOSURES FOR CONTAINERS

CROSS-REFERENCE TO RELATED APPLICATION

This application claims priority to Italian Patent Application No. 102022000023250 filed on Nov. 10, 2022, the disclosure of which is incorporated herein by this reference in its entirety.

FIELD

The present invention relates to a treatment apparatus for treating closures for containers.

BACKGROUND

In an aseptic bottling line, before filling and capping the formed containers, there is also a need to sterilize the closures (caps or capsules) of the containers themselves. In the prior art, the closures can be sterilized either using chemical agents, or with electromagnetic radiation.

SUMMARY

A treatment apparatus for treating closures for containers. The treatment apparatus includes a box-like body and a treating chamber inside the box-like body. The treating chamber configured for treating the closures. The treatment apparatus further includes a dispensing pipe located inside the treating chamber and configured to dispense a sterilizing substance and a supplying circuit configured to supplying the sterilizing substance. The supplying circuit including a feeding line, a main line, and a secondary line. Both the main line and the secondary line branching-off from the feeding line and the main line emerging into the dispensing pipe and the secondary line emerging inside the box-like body. The treatment apparatus further includes one or more valves operatively active on the supplying circuit to establish a selective fluid communication between the feeding line and the main line or between the feeding line and the secondary line.

BRIEF DESCRIPTION OF THE DRAWINGS

Further features and advantages of the present invention will become more apparent from the following approximate, and hence non-limiting, description of a preferred, but not exclusive, embodiment of a treatment apparatus for treating closures for containers, as illustrated in the appended drawings, in which.

DESCRIPTION OF EMBODIMENTS

Figure 1:
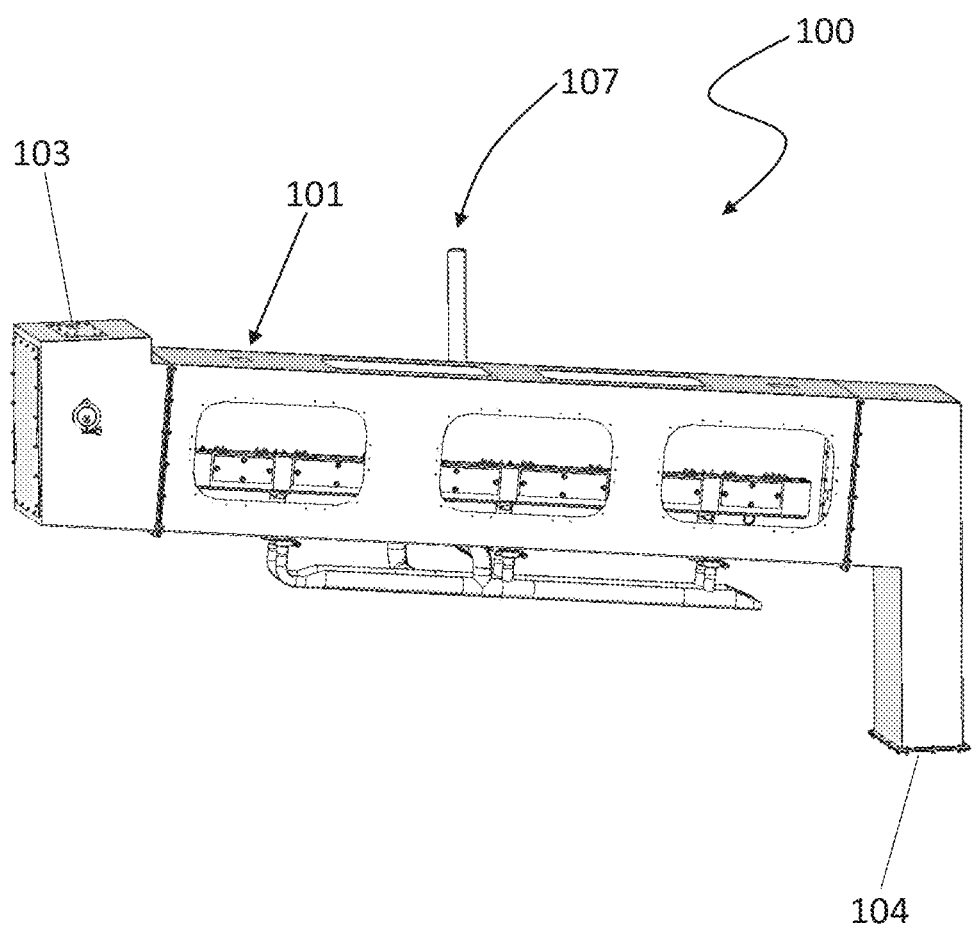
FIGS. 1 and 2 illustrate two different perspective views a treatment apparatus for treating closures for containers.

The present disclosure concerns sterilization of closures using chemical agents. Closures can be sterilized either using chemical agents, or with electromagnetic radiation.

For example, an apparatus for treating closures with a sterilizing agent within a rotating unit having a plurality of longitudinal rails where the closures are fed by force of gravity is previously known and is described in detail in the international application WO 2014/140948.

Another solution consists in an inclined channel for conveying the closures towards the capping unit, where the closures advance by force of gravity. A stop event occurring downwards (for example involving the bottles) or within the treatment apparatus, results in the closures being stuck in the rotating unit of the treatment apparatus or in the inclined channel.

In order to prevent deformation of the closures due to a prolonged exposure to the sterilizing agent, supplying of the sterilizing agent is usually interrupted or at least reduced. In fact, deformation of the closures may affect their application on the mouth of the containers.

Nevertheless, interrupting the supply of the sterilizing agent raises issues in controlling the process. As a matter of fact, when the stop event is resolved it is necessary to restart the process by correctly resetting the parameters. These operations require a transient time which is not neglectable and has a negative impact on the overall equipment effectiveness.

In this context, the technical task at the basis of the present disclosure is to propose a treatment apparatus for treating closures for containers, which helps to overcome the problems discussed.

In some embodiments, an object of the present disclosure is to provide a treatment apparatus for treating closures for containers, which is able to deal with stop events in a quicker and more reliable way than previous solutions.

The stated technical task and specified objects are substantially achieved by a treatment apparatus for treating closures for containers, the treatment apparatus comprising:
  a box-like body;
  a treating chamber for the closures inside the box-like body;
  a dispensing pipe located inside the treating chamber and configured to dispense a sterilizing substance;
  a supplying circuit for supplying the sterilizing substance, the supplying circuit comprising a feeding line,
characterized in that the supplying circuit further comprises:
  a main line and a secondary line, both the main line and the secondary line branching-off from the feeding line, the main line emerging into the dispensing pipe and the secondary line emerging inside the box-like body;
  one or more valves operatively active on the supplying circuit so as to establish a selective fluid communication between the feeding line and the main line or between the feeding line and the secondary line.

In some embodiments, the one or more valves comprises at least two valves.

In some embodiments, the treatment apparatus further comprises a compartment located inside the box-like body and delimiting the treating chamber.

The secondary line emerges inside the box-like body out of the compartment.

In some embodiments, the dispensing pipe comprises a plurality of nozzles.

In some embodiments, the nozzles are located close to the conveying path.

In some embodiments, the nozzles are inclined towards an advancement direction of the closures along the conveying path.

In some embodiments, the secondary line is designed to reproduce the overall flow resistance of the main line and of the dispensing pipe.

In some embodiments, the one or more valves are configured to set the treatment apparatus in one of the following configurations:

a working configuration in which the one or more valves establish a fluid communication between the feeding line and the main line so that the dispensing pipe is supplied with the sterilizing substance, the one or more valves interrupting the fluid communication between the feeding line and the secondary line, and an idle configuration in which the one or more valves establish a fluid communication between the feeding line and the secondary line so that the sterilizing substance is discharged inside an environment delimited by the box-like body, the one or more valves interrupting the fluid communication between the feeding line and the main line.

In some embodiments, the box-like body has a substantially tubular shape, and the compartment consists in a tunnel.

The treatment apparatus further comprises at least one conveying path developing inside the tunnel along which the closures linearly advance.

In some embodiments, the main line has a plurality of intakes connected to the dispensing pipe.

The secondary line has a plurality of intakes emerging inside the box-like body and outside the tunnel.

In some embodiments, the main line and the secondary line have corresponding linear tracts that are substantially parallel to each other.

In some embodiments, the treatment apparatus further comprises:— a plurality of conveying paths inside the treating chamber;
a plurality of dispensing pipes, one for each of said conveying paths.

In some embodiments, the supplying circuit comprises a plurality of main lines branching-off from the feeding line. Each main line of the plurality of said main lines emerges into one corresponding dispensing pipe of the plurality of said dispensing pipes.

In some embodiments, the box-like body has a substantially drum shape.

The treatment apparatus further comprises a rotating carousel located in the treating chamber and plurality of longitudinal rails for housing the closures arranged by force of gravity. The rails are substantially parallel to one another and are integrally connected to the rotating carousel.

The disclosure finds application in the field of bottling using aseptic technology. Another possible application is in the extended shelf-life technology.

With reference to the figures, reference numeral 100 denotes a treatment apparatus, using a sterilizing substance, for treating closures 2 for containers.

In this context, the term closure 2 relates to a concave closure such as a cap or a capsule. The closure 2 is preferably made of a polymer material.

Figure 4:
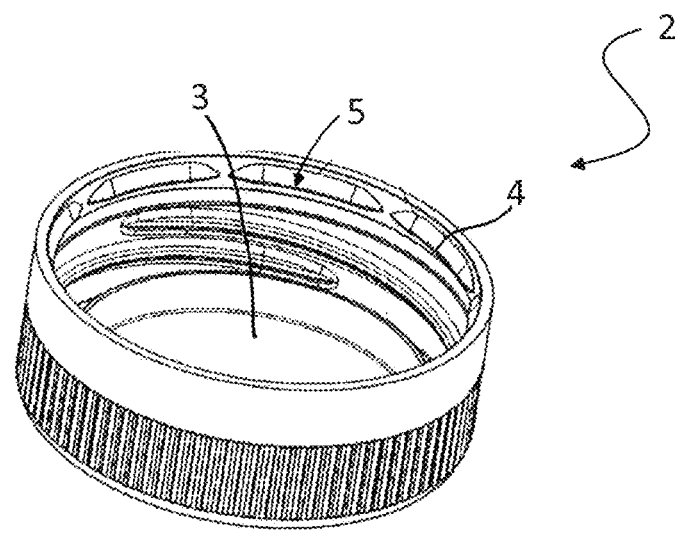
FIG. 4 illustrates a flat cap according to the prior art.

For example, the closure 2 is represented by a flat cap, as illustrated in FIG. 4. Another example of a closure 2 is represented by a sports cap shown in FIG. 5.

In both cases, the closure 2 has a base 3 and a lateral wall 4 extending from the base 3 and defining therewith a cavity 5. The cavity 5 is open: in fact, on the side opposite the base 3 the closure 2 has an opening that can accommodate the mouth of a container so that the lateral wall 4 can engage therewith and the base 3 can close it. In this context, the term "internal surfaces" of the closure 2 identifies the internal surface of the lateral wall 4 and the internal surface of the base 3. The term "external surfaces" of the closure 2 refers to the external surface of the lateral wall 4 and the external surface of the base 3.

In FIG. 4 the cavity 5 delimited by the closure 2 exhibits a substantially cylindrical shape, so that the lateral wall 4 corresponds substantially to the lateral wall of a cylinder and the base 3 is a circular disc. Alternatively, the cavity 5 delimited by the closure 2 has a slightly conical shape.

Figure 5:
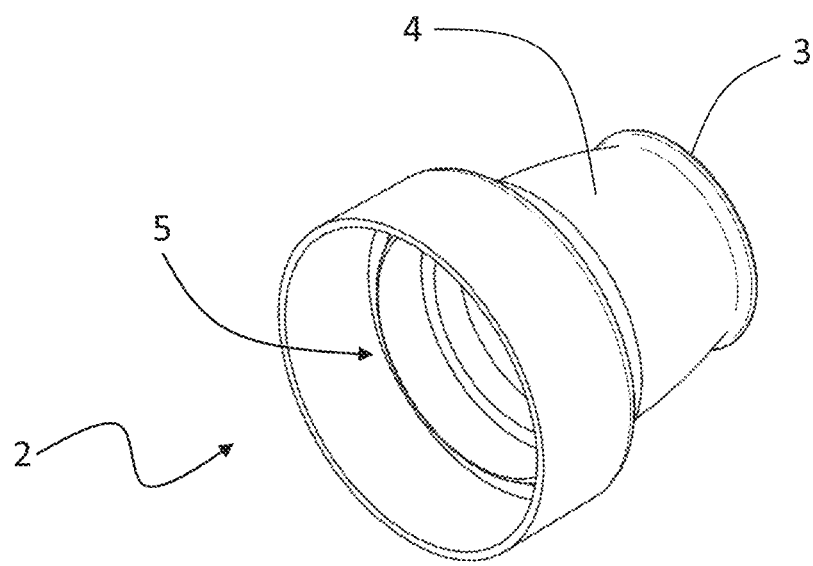
FIG. 5 illustrates a sports cap according to the prior art.

The sports cap 2 of FIG. 5 exhibits a more complex shape, though the base 3, the lateral wall 4 and the cavity 5 can also be identified therein.

The treatment apparatus 100 comprises a box-like body 101 delimiting an environment 102.

Inside the box-like body 101 there is a compartment 114 defining a treating chamber 115 for the closures 2

In some embodiments, illustrated herewith, the treatment apparatus 100 is of the linear type.

In the first embodiment, the box-like body 101 has a substantially tubular shape. The environment 102 defined by the tubular box-like body 101 is therefore shaped as a channel.

In some embodiments, the compartment 114 consists in a tunnel (which is also indicated as 114 in the following description).

The treatment apparatus 100 further comprises at least one conveying path 116 inside the treating chamber 115.

The closures 2 are made to advance linearly, e.g., one after the other, along the conveying path 116. In some embodiments, the conveying path 116 may be defined by rails.

In the linear-type treatment apparatus 100, the box-like body 101 has an inlet 103 receiving the closures 2 to be treated and an outlet 104 delivering the treated closures 2 to the capping unit located downstream.

Figure 2:
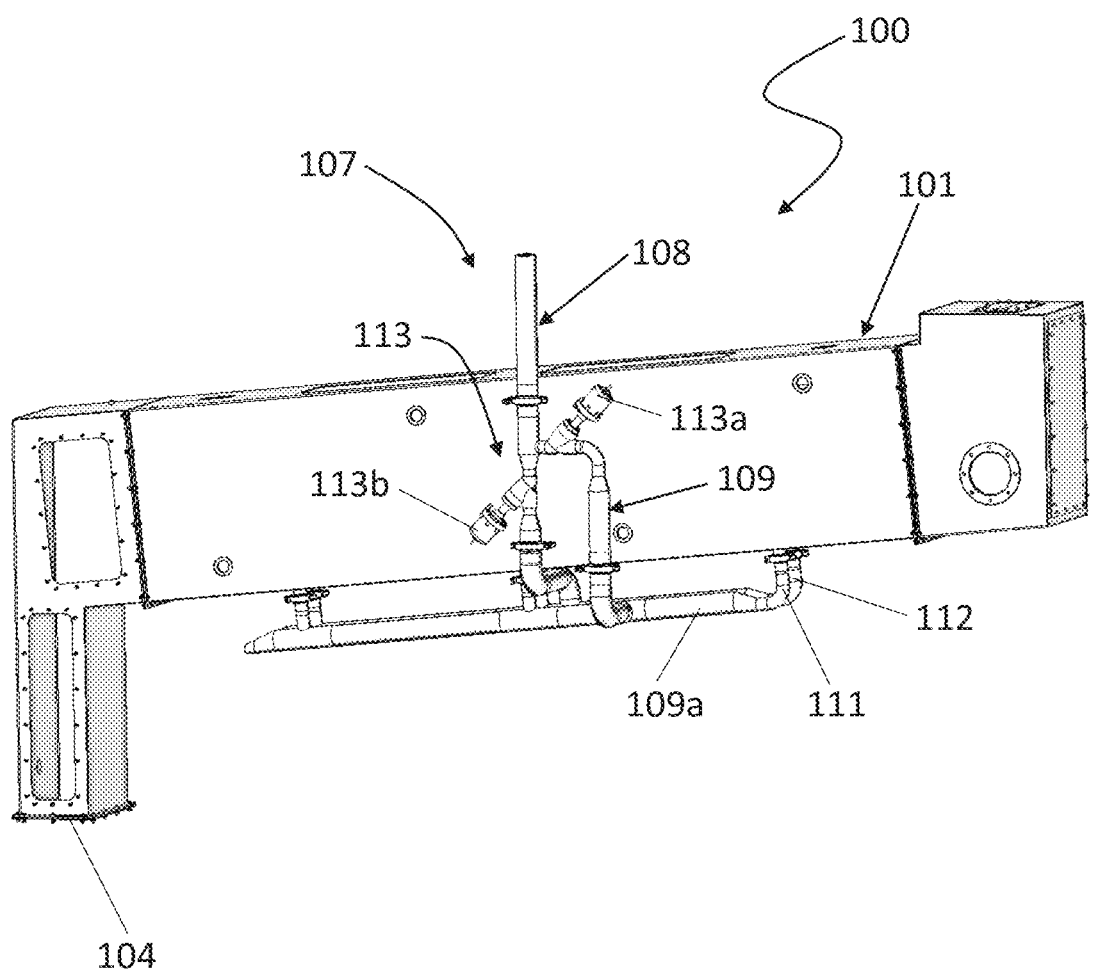
Figure 3:
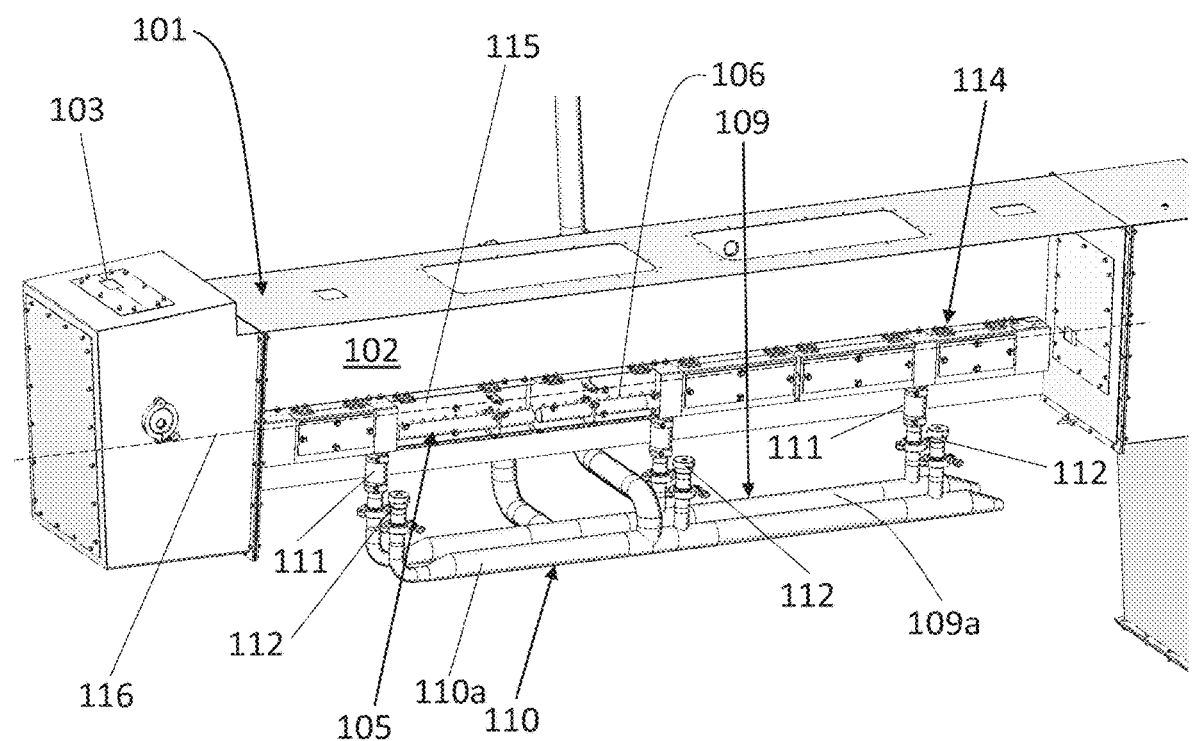
FIG. 3 is a zoom view of a detail of the treatment apparatus of FIG. 1, where part of the box-like body is removed for the sake of comprehension.

The box-like body 101 is preferably inclined, as illustrated in FIGS. 1-2.

Thus, the closures 2 advance along the conveying path 116 by force of gravity and/or by force of gas jet that can be the sterilizing substance.

The treatment apparatus 100 further comprises a dispensing pipe 105 configured to dispense a sterilizing substance and located inside the treating chamber 115.

For example, the sterilizing substance is hydrogen peroxide. In some embodiments, the sterilizing substance is gaseous. Alternatively, the sterilizing sub stance is liquid.

In some embodiments, disclosed and illustrated herewith, the dispensing pipe 105 is an elongated pipe developing inside the tubular box-like body 101.

Thus, in some embodiments the dispensing pipe 105 has a substantially longitudinal extension inside the tunnel 114.

In some embodiments, the dispensing pipe 105 comprises a plurality of nozzles 106 that are also located inside the treatment chamber 115.

In some embodiments, the nozzles 106 are distributed along the length of the dispensing pipe 105.

In some embodiments, the nozzles 106 are equally spaced along the length of the dispensing pipe 105.

In some embodiments, the nozzles 106 are located below the conveying path 116 so that the closures 2 are hit from below by the sterilizing substance dispensed by the nozzles 106 during the normal operation of the treatment apparatus 100, as it will be explained later.

In some embodiments, the nozzles 106 are located above or laterally to the conveying path 116.

In some embodiments, the nozzles 106 are arranged closed to the conveying path 116 so that the closures 2 advancing along the conveying path 116 receive the sterilizing substance.

In some embodiments, the nozzles 106 are inclined towards the advancement direction of the closures 2 along the conveying path 116.

In some embodiments, the nozzles 106 are arranged so that their dispensing direction is oriented towards the conveying path 116 and, thus to the closures 2 advancing there along.

In some embodiments, the dispensing pipe 105 is located in a zone of the treating chamber 115, emerging therein.

The treatment apparatus 100 comprises a supplying circuit 107 for supplying the sterilizing substance.

The supplying circuit 107 comprises at least a feeding line 108, a main line 109 and a secondary line 110.

The main line 109 and the secondary line 110 branch-off from the feeding line 108. The main line 109 emerges into the dispensing pipe 105.

In some embodiments, the main line 109 has a plurality of intakes 111 connected to the dispensing pipe 105.

The intakes 111 of the main line 109 are distributed along the length of the dispensing pipe 105 so as to uniformly supply the sterilizing substance to the dispensing pipe 105.

The secondary line 110 emerges into the environment 102.

In some embodiments, the secondary line 110 has a plurality of intakes 112 emerging into the environment 102.

The intakes 112 of the secondary line 110 are distributed along the length of environment 102 so as to reproduce the layout of the main line 109.

The intakes 112 of the secondary line 110 are arranged outside the tunnel 114.

In some embodiments, the intakes 112 of the secondary line 110 are arranged at a higher distance from the conveying path 116 with respect to the nozzles 106.

The secondary line 110 is designed to reproduce the overall flow resistance of the main line 109 and of the dispensing pipe 105.

In some embodiments, the secondary line 110 is designed to reproduce the overall flow resistance of the main line 109 with its intakes 111 and of the dispensing pipe 105 with the nozzles 106.

The treatment apparatus 100 comprises one or more valves 113 that are operatively active on the supplying circuit 107 so as to establish a selective fluid communication between the feeding line 108 and the main line 109 or between the feeding line 108 and the secondary line 110.

In some embodiments, the one or more valves 113 are configured to set the treatment apparatus 100 in one of the following configurations: a working configuration or an idle configuration.

In the working configuration the one or more valves 113 establish a fluid communication between the feeding line 108 and the main line 109 so that the dispensing pipe 105 is supplied with the sterilizing substance.

Thus, the nozzles 106 dispense the sterilizing substance on the closures 2 that are advancing in the treating chamber 115 along the conveying path 116.

In the working configuration, the one or more valves 113 prevent the fluid communication between the feeding line 108 and the secondary line 110.

Therefore, in the working configuration the secondary line 110 does not discharge any sterilizing substance into the environment 102.

In the idle configuration the one or more valves 113 establish a fluid communication between the feeding line 108 and the secondary line 110 so that the sterilizing substance is discharged directly inside the environment 102.

In the idle configuration the one or more valves 113 interrupt the fluid communication between the feeding line 108 and the main line 109.

Therefore, the nozzles 106 do not dispense the sterilizing substance on the closures 2 inside the treatment chamber 115.

In some embodiments, the tunnel 114 cannot be tight-sealed, thus the treatment chamber 115 is not physically separated from the environment 102.

Nevertheless, the tunnel 114 serves for preventing the sterilizing substance from spreading away from the closures 2 during the working configuration, and to limit high quantity of sterilizing substance discharged from the secondary line 110 from reaching the closures 2 during the idle configuration.

In some embodiments, the one or more valves 113 comprises at least two valves 113a, 113b, that are a first valve 113a operatively active on the main line 109 and a second valve 113b operatively active on the secondary line 110.

When the treatment apparatus 100 is set in the working configuration, the first valve 113a is open so that the sterilizing substance may flow from the feeding line 108 to the main line 109, whereas the second valve 113b is closed so that the flow of sterilizing substance from the feeding line 108 to the secondary line 110 is interrupted.

When the treatment apparatus 100 is set in the idle configuration, the second valve 113b is open so that sterilizing substance may flow from the feeding line 108 to the secondary line 110, whereas the first valve 113a is closed so that the flow of the sterilizing substance from the feeding line 108 to the main line 109 is interrupted. In some embodiments, the main line 109 and the secondary line 110 have corresponding linear tracts 109a, 110a that are substantially parallel to each other. These linear tracts 109a, 110a develop substantially parallel to the tubular box-like body 101.

In some embodiments, these linear tracts 109a, 110a are located under the box-like body 101.

Nevertheless, these linear tracts 109a, 110a may be located above the box-like body 101.

In some embodiments, the treatment apparatus 100 comprises a plurality of conveying paths 116 inside the treating chamber 114.

In some embodiments, more conveying paths 116 are used with closures 2 of different types, for example flat caps and sports caps.

For example, flat caps are made to advance on a first conveying path 116, whereas sports caps are made to advance on a second conveying path 116.

In some embodiments, the treatment apparatus 100 comprises two dispensing pipes 105 with corresponding nozzles 106: a first dispensing pipe 105 configured to dispense the sterilizing substance on the flat caps and a second dispensing pipe 105 configured to dispense the sterilizing substance on the sports caps.

Accordingly, the supplying circuit 107 comprises two main lines 109 (a first and a second main line) and one secondary line 110.

The main lines 109 and the secondary line 110 branch-off from the feeding line 108.

The first main line 109 emerges into the first dispensing pipe 105.

The second main line 109 emerges into the second dispensing pipe 105.

The two dispensing pipes 105 and the two conveying paths 116 are under the same tunnel 114. Alternatively, there may be a tunnel 114 for each dispensing pipe 105 and conveying path 116.

In some embodiments, the main lines 109 are designed to be different for treating different types of closures 2.

In some embodiments, the main lines 109 are identical.

The secondary line 110 is designed to reproduce the overall flow resistance of the first main line 109 and of the first dispensing pipe 105.

In some embodiments, the secondary line 110 is designed to reproduce the overall flow resistance of the main line 109 with their intakes 111 and of the dispensing pipes 105 with their nozzles 106.

The secondary line 110 emerges in the environment 102, outside the tunnel 114 or tunnels 114.

In some embodiments, the treatment apparatus 100 comprises two conveying paths 116 inside the treating chamber 115, each with its own dispensing pipe 105, but there are only one main line 109 and one secondary line 110.

For example, the conveying paths 116 are respectively for flat caps and for sports caps.

In some embodiments, the main line 109 emerges into the dispensing pipe 105 relative to the flat cap, while the secondary line 110 emerges into the dispensing pipe 105 relative to the sports cap, or vice versa.

In some embodiments, the two dispensing pipes 105 are located inside two different tunnels 114.

Therefore, when the treatment apparatus 100 is functioning with flat caps and is in the idle configuration, the sterilizing substance may be discharged by the secondary line 110 inside the tunnel 114 of the sports caps, so that the flat caps are preserved (they are under their own tunnel 114).

On the contrary, when the treatment apparatus 100 is functioning with sports caps and is in the idle configuration, the sterilizing substance may be discharged by the main line 109 inside the tunnel 114 of the flat caps, so that the sports caps are preserved (they are under their own tunnel 114).

In other words, the main line 109 and the secondary line 110 can exchange their role depending on the needs.

In some embodiments (not illustrated), the treatment apparatus 100 is of the rotating type.

The treatment apparatus 100 comprises a box-like body 101 that has a substantially drum shape delimiting the environment 102.

The treatment apparatus 100 further comprises a rotating carousel located in the treating chamber 115 and plurality of longitudinal rails for housing the closures 2 arranged by force of gravity. The rails are substantially parallel to one another and are integrally connected to the rotating carousel.

The functioning of the treatment apparatus for treating closures for containers according to some embodiments is described below with reference to the linear-type apparatus.

When the treatment apparatus 100 is set in the working configuration, the first valve 113a is open so that the sterilizing substance may flow from the feeding line 108 to the main line 109 and thus to the dispensing pipe 105.

The closures 2 continuously advance in the treating chamber 115 along the conveying path 116. While advancing, the closures 2 are subject to the sterilizing substance that is dispensed by the nozzles 106 of the dispensing pipe 105.

Since the nozzles 106 are inclined in the advancement direction of the closures 2 along the conveying path 116, the sterilizing substance is dispensed directly towards the closures 2.

In this configuration, the secondary line 110 is not used. In fact, the second valve 113b is closed so there is no flow of sterilizing substance from the feeding line 108 to the secondary line 110.

In case of a fault occurring downstream the treatment apparatus 100 or in case of a stop event occurring inside the treatment apparatus 100, the continuous flow of the closures 2 along the conveying path 116 is interrupted.

The treatment apparatus 100 is thus set in the idle configuration, in which the first valve 113a is closed so that the nozzles 106 stop to dispense the sterilizing substance to the closures 2.

In this configuration, the second valve 113b is open so that the sterilizing substance that should have been supplied to the main line 109 is now supplied to the secondary line 110. In practice, the secondary line 110 acts as a by-pass line that is activated in case of a fault.

The secondary line 110 discharges the sterilizing substance inside the environment 102 by means of its intakes 112.

As already explained, the intakes 112 of the secondary line 110 are located outside the tunnel 114.

Thus, the sterilizing substance exiting from the intakes 112 of the secondary line 110 is not directed towards the closures 2 inside the treating chamber 115 but merely spreads in the environment 102.

The closures 2 are thus prevented from being directly hit by the sterilizing substance.

By designing the secondary line 110 with the same flow resistance of the main line 109 and of the dispensing pipe 105, the units located upstream the treatment apparatus 100 are not affected by faults. The process parameters do not need to be adjusted in response to faults.

The functioning of the rotary apparatus is analogous.

The characteristics of the treatment apparatus for treating closures for containers, according to some embodiments, prove to be clearly indicated in the description provided.

In case of a fault downstream or within the treatment apparatus the sterilizing substance is merely diverted to the secondary line that acts as a by-pass line.

There is no need to interrupt the supply of the sterilizing substance, as it occurred in prior solutions. It is sufficient to divert the flow of the sterilizing substance in the secondary line.

The sterilizing substance is discharged in the treating chamber, but not directly on the closures. Thus, the closures that are stuck in the channel are not directly exposed to the sterilizing substance.

This prevents or at least reduces their deformation.

Therefore, the disclosure treatment apparatus may be more likely to properly sterilize the closures and at the same time contribute to maintain their original shape, that is best for a correct application on the containers.

In addition, because the flow resistance of the secondary line is the same of the main line and of the dispensing pipe, the overall parameters of the process may not be affected.

As a result, there is no need or a reduced need to adjust the process parameters during the stop and to restart the plant when the fault is resolved.

The treatment apparatus proposed overcomes or helps to overcome the needs of transient time for adjusting and restarting the process parameters in case of a fault.

Terms used herein and especially in the appended claims (e.g., bodies of the appended claims) are generally intended as "open" terms (e.g., the term "including" should be interpreted as "including, but not limited to," the term "having" should be interpreted as "having at least," the term "includes" should be interpreted as "includes, but is not limited to," etc.).

Additionally, if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations.

In addition, even if a specific number of an introduced claim recitation is explicitly recited, it is understood that such recitation should be interpreted to mean at least the recited number (e.g., the bare recitation of "two recitations," without other modifiers, means at least two recitations, or two or more recitations). Furthermore, in those instances where a convention analogous to "at least one of A, B, and C, etc." or "one or more of A, B, and C, etc." is used, in general such a construction is intended to include A alone, B alone, C alone, A and B together, A and C together, B and C together, or A, B, and C together, etc. For example, the use of the term "and/or" is intended to be construed in this manner.

Further, any disjunctive word or phrase presenting two or more alternative terms, whether in the description, claims, or drawings, should be understood to contemplate the possibilities of including one of the terms, either of the terms, or both terms. For example, the phrase "A or B" should be understood to include the possibilities of "A" or "B" or "A and B."

Additionally, the use of the terms "first," "second," "third," etc., are not necessarily used herein to connote a specific order or number of elements. Generally, the terms "first," "second," "third," etc., are used to distinguish between different elements as generic identifiers. Absence a showing that the terms "first," "second," "third," etc., connote a specific order, these terms should not be understood to connote a specific order. Furthermore, absence a showing that the terms first," "second," "third," etc., connote a specific number of elements, these terms should not be understood to connote a specific number of elements. For example, a first widget may be described as having a first side and a second widget may be described as having a second side. The use of the term "second side" with respect to the second widget may be to distinguish such side of the second widget from the "first side" of the first widget and not to connote that the second widget has two sides.

All examples and conditional language recited herein are intended for pedagogical objects to aid the reader in understanding the and the concepts contributed by the inventor to furthering the art, and are to be construed as being without limitation to such specifically recited examples and conditions. Although embodiments of the present disclosure have been described in detail, it should be understood that the various changes, substitutions, and alterations could be made hereto without departing from the spirit and scope of the present disclosure.

The invention claimed is:

1. A treatment apparatus for treating closures for containers, the treatment apparatus comprising:
    a box-like body;
    a treating chamber inside the box-like body, the treating chamber configured for treating the closures;
    a dispensing pipe located inside the treating chamber and configured to dispense a sterilizing substance;
    a supplying circuit configured to supplying the sterilizing substance, the supplying circuit including:
        a feeding line;
        a main line; and
        a secondary line, both the main line and the secondary line branching-off from the feeding line and the main line emerging into the dispensing pipe and the secondary line emerging inside the box-like body; and
    one or more valves operatively active on the supplying circuit to establish a selective fluid communication between the feeding line and the main line or between the feeding line and the secondary line,
    wherein said secondary line is designed to reproduce an overall flow resistance of the main line and of the dispensing pipe, and
    the one or more valves are configured to set the treatment apparatus in one of the following configurations:
        a working configuration in which the one or more valves establishes a fluid communication between the feeding line and the main line so that the dispensing pipe is supplied with the sterilizing substance and in the working configuration the one or more valves interrupt the fluid communication between the feeding line and the secondary line, and
        an idle configuration in which the one or more valves establish a fluid communication between the feeding line and the secondary line so that the sterilizing substance is discharged inside an environment delimited by the box-like body and in the idle configuration the one or more valves interrupt the fluid communication between the feeding line and the main line.

2. The treatment apparatus according to claim 1, further comprising a compartment located inside the box-like body and delimiting said treating chamber, the secondary line emerging inside the box-like body out of the compartment.

3. The treatment apparatus according to claim 2, wherein the box-like body has a substantially tubular shape, the compartment consists in a tunnel, and the treatment apparatus further comprises at least one conveying path developing inside the tunnel along which the closures linearly advance.

4. The treatment apparatus according to claim 3, wherein the main line has a plurality of intakes connected to said dispensing pipe.

5. The treatment apparatus according to claim 3, wherein the secondary line has a plurality of intakes emerging inside the box-like body and outside the tunnel.

6. The treatment apparatus according to claim 3, wherein said dispensing pipe comprises a plurality of nozzles.

7. The treatment apparatus according to claim 6, wherein said nozzles are located close to the conveying path.

8. The treatment apparatus according to claim 7, wherein said nozzles are inclined towards an advancement direction of the closures along the conveying path.

9. The treatment apparatus according to claim 3, wherein the main line and the secondary line have corresponding linear tracts that are substantially parallel to each other.

10. The treatment apparatus according to claim 1, wherein the one or more valves comprises at least two valves.

\* \* \* \* \*